United States Patent
Butler

(10) Patent No.: US 7,325,444 B2
(45) Date of Patent: Feb. 5, 2008

(54) METHODS AND SYSTEMS FOR DETERMINING MOISTURE TRANSFER CHARACTERISTICS OF WELDING MATERIALS

(75) Inventor: Kevin Butler, Broadview Heights, OH (US)

(73) Assignee: Lincoln Global, Inc., City of Industry, CA (US)

( * ) Notice: Subject to any disclaimer, the term of this patent is extended or adjusted under 35 U.S.C. 154(b) by 9 days.

(21) Appl. No.: 11/284,348

(22) Filed: Nov. 21, 2005

(65) Prior Publication Data

US 2007/0113689 A1 May 24, 2007

(51) Int. Cl.
*G01N 5/02* (2006.01)
(52) U.S. Cl. .......................................................... 73/73
(58) Field of Classification Search ...................... None
See application file for complete search history.

(56) References Cited

U.S. PATENT DOCUMENTS

| | | | |
|---|---|---|---|
| 3,751,626 A | * | 8/1973 | Binger et al. ................ 219/118 |
| 3,905,234 A | * | 9/1975 | Berghof ...................... 73/865.6 |
| 4,142,403 A | * | 3/1979 | Lohnes et al. .................. 73/76 |
| 4,426,428 A | * | 1/1984 | Kammer et al. ............. 428/561 |
| 4,517,441 A | * | 5/1985 | Kaljee et al. ........... 219/146.23 |
| 4,620,799 A | * | 11/1986 | Palazzetti et al. ............... 374/5 |
| 5,393,426 A | * | 2/1995 | Raskin et al. ................ 210/602 |
| 5,435,206 A | * | 7/1995 | Gunnell et al. ............... 73/866 |
| 5,983,711 A | * | 11/1999 | Pappas et al. .................. 73/76 |
| 6,114,680 A | * | 9/2000 | Bank et al. .................. 219/731 |

OTHER PUBLICATIONS

Definition of "Item" from American Heritage Dictionary, 1984.*

* cited by examiner

*Primary Examiner*—Robert Raevis
(74) *Attorney, Agent, or Firm*—Fay Sharpe LLP

(57) ABSTRACT

Systems and methods are presented for determining a transfer characteristic of welding electrodes, flux, or other welding consumable, or materials used in producing welding consumables, in which an analytical scale or other weight measurement instrument is situated within an environmental chamber to weigh welding consumable test items while the atmospheric conditions inside the chamber are controlled. A data acquisition system is located outside the chamber and is operatively coupled with the scale to obtain a number of measurements at different times while the atmospheric condition in the interior of said environmental chamber is controlled to a test condition.

8 Claims, 3 Drawing Sheets

METHODS AND SYSTEMS FOR DETERMINING MOISTURE TRANSFER CHARACTERISTICS OF WELDING MATERIALS

FIELD OF THE INVENTION

The present invention relates generally to the welding arts and more particularly to measurement systems and methods for determining moisture transfer characteristics of welding consumables.

BACKGROUND

Welding consumables include flux products, welding wire or electrodes, and other materials that are consumed during a welding process. In the manufacture and use of such welding consumables, it is sometimes desirable to measure and control the moisture, carbon dioxide ($CO_2$) content, or content of other material such as nitrogen (N), etc., of the consumable, as well as the propensity of the consumable to absorb or release moisture or other elements or materials (e.g., N, $CO_2$), since these characteristics may affect the welding process and the ultimate weld joint created thereby. Furthermore, the amount of moisture absorbed by welding flux and electrodes is important, as moisture on or in either can lead to substandard weld properties. It is thus desirable for welding consumable suppliers to characterize the moisture content (and $CO_2$ content) and absorption rates for these products, for both the design and development of new products and for quality control purposes during manufacturing. The moisture transfer characteristics can be determined by weight measurements before and after exposure of a welding consumable to a humid (or arid) environment.

In order to adequately characterize the absorption tendencies, conventional practice has been to initially weigh a sample and to thereafter place the sample in an environmental chamber with controlled temperature and humidity. After exposure to the controlled atmospheric conditions for a certain amount of time, the test sample is removed from the chamber and again weighed, where the change in weight is indicative of the amount of moisture gained (or lost), and the weight change and the exposure time can be correlated to estimate an absorption rate.

As the moisture absorption transfer characteristics of welding consumables (and/or raw materials used in the production thereof) is a function of time, it is generally desirable to measure the transfer effects at a number of different times. For instance, testing positive moisture absorption (gain) at a given set of chamber humidity and temperature conditions may be done for an extended time period, such as 24 hours. In order to obtain a spread in the measured data, exposure times of 0, 1, 2, 4, 6, 8, 10, 12, 18, and 24 hours may be selected, where ten samples are initially measured and placed in the environmental test chamber. After one hour of humidity exposure, the chamber door is opened and one sample is removed and weighed to obtain a first data point. A second sample is removed an hour later and weighed, and this process continues with samples being removed and weighed at 4, 6, 8, 10, 12, 18, and 24 hours to complete the test. While this approach obtains a 24 hour spread of data in a single day of testing, test personnel must be present at each selected time period to remove and weigh a sample. Furthermore, the humidity exposure environment is disturbed by opening and closing the chamber door every time a sample is removed for weighing. Also, the samples may lose a significant amount of acquired moisture while being transported from the environmental chamber to the weighing station. Alternatively, a first sample could be tested alone for 1 hour, with a second sample being tested alone for 2 hours, and so on, with the final sample being tested alone for 24 hours. This approach may advantageously provide for undisturbed exposure of the tested samples throughout the entire test until removal for weighing. However, the test chamber is occupied for over 80 hours, and requires test personnel to be present to start a new test as each prior test is completed. Choosing between these conventional methods is thus a tradeoff between obtaining erroneous data because of atmospheric disturbance when removing a sample from the environmental chamber and increased testing cost by occupying the chamber for long periods of time. Moreover, in each approach, a consumable product sample is needed for each data point, and the interim moisture transfer behavior between test points is not measured. Furthermore, the addition of more test points necessitates usage of more samples and either further intermediate disturbance or longer allocation of test chamber resources. Thus, there is a need for improved methods and measurement systems for determining transfer characteristics of welding consumables.

SUMMARY

Various aspects of the invention are hereinafter summarized in order to facilitate a basic understanding thereof, wherein this summary is not an extensive overview of the invention, and is intended neither to identify certain elements of the invention, nor to delineate the scope of the invention. Rather, the primary purpose of the summary is to present some concepts of the invention in a simplified form before a more detailed description is presented below. The present invention is related to measurement systems and methodologies employing an analytical balance or other weight measurement instrument and an atmosphere-controlled chamber, by which one or more transfer characteristics of a welding consumable product or component material may be quantified or determined. The balance instrument is located inside a controlled-atmosphere enclosure or chamber, and transmits data to a data collection device outside the chamber, allowing collection of real-time absorption or release properties in a variety of atmospheres, where the data may be acquired periodically or continuously to provide high time resolution to capture short term material transfer characteristics of a tested welding consumable.

BRIEF DESCRIPTION OF THE DRAWINGS

The following description and drawings set forth certain illustrative implementations of the invention in detail, which are indicative of several exemplary ways in which the principles of the invention may be carried out. Other objects, advantages and novel features of the invention will become apparent from the following detailed description of the invention when considered in conjunction with the drawings, in which.

DETAILED DESCRIPTION OF A PREFERRED EMBODIMENT OF THE INVENTION

Figure 1:
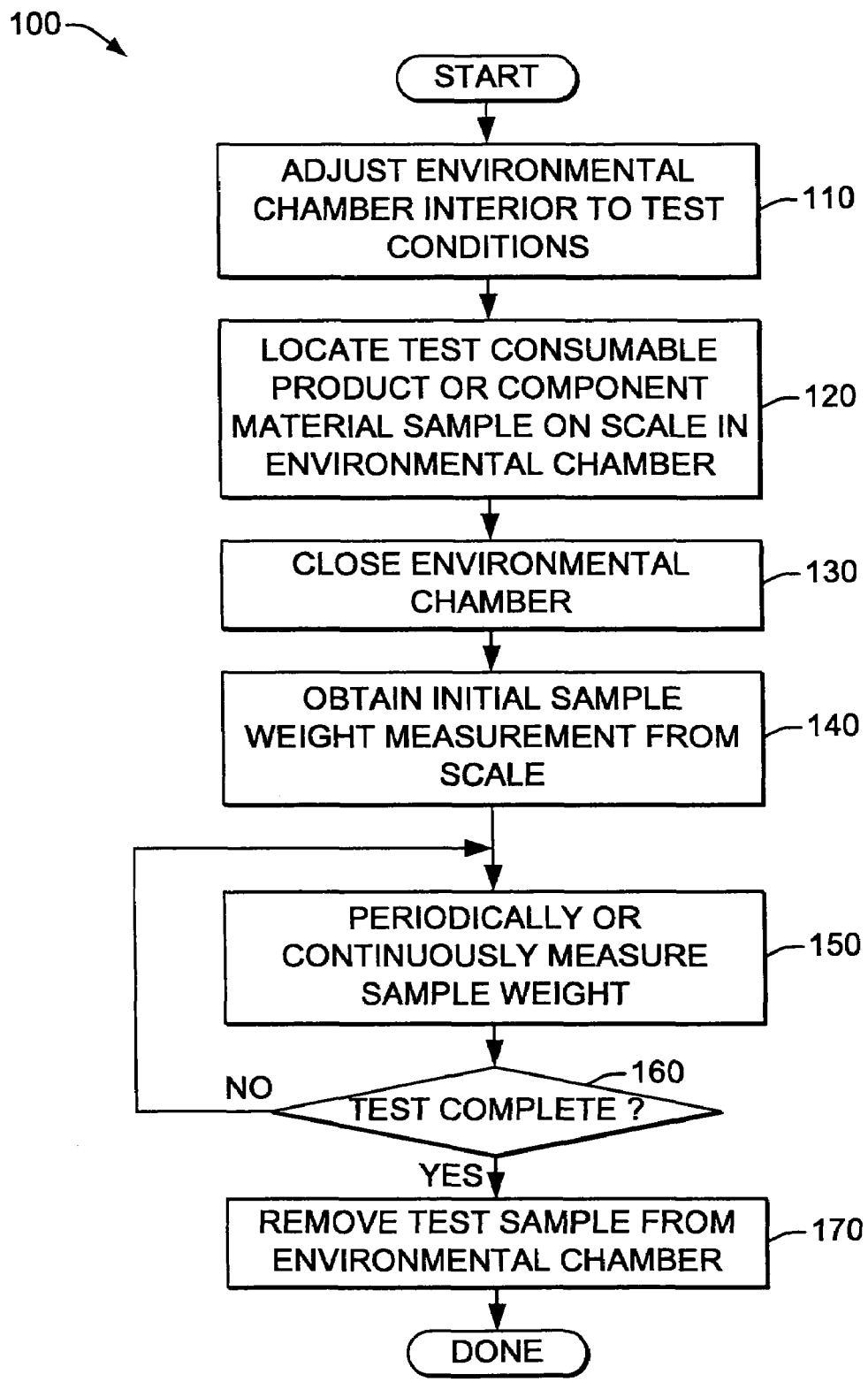
FIG. 1 is a flow diagram illustrating an exemplary method for determining a transfer characteristic of a welding consumable or component material in accordance with one or more aspects of the invention.
Figure 2:
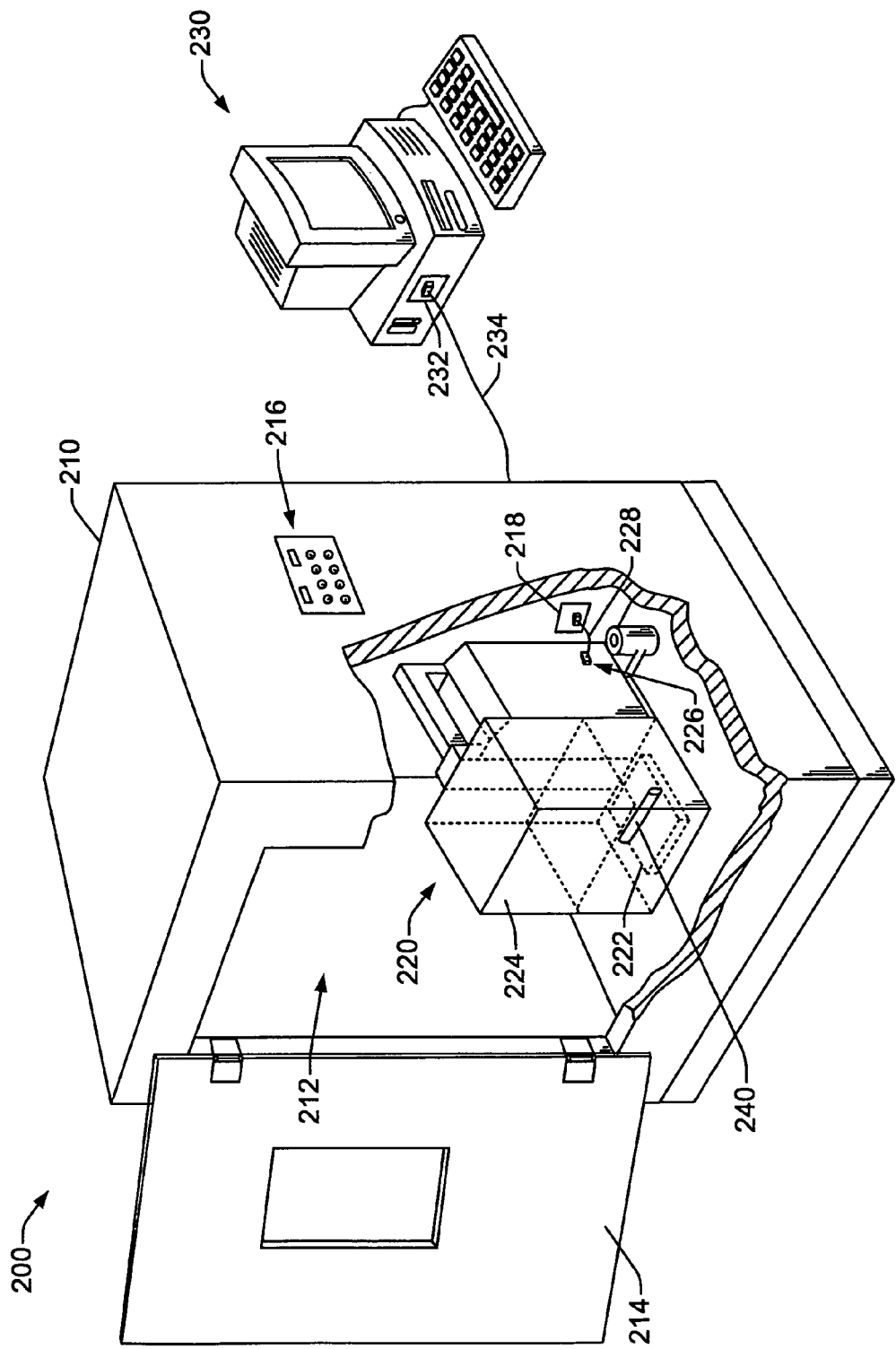
FIG. 2 is a simplified perspective drawing illustrating a system for testing a welding consumable product or material used in the fabrication of welding consumables in accordance with the invention.

Referring initially to FIGS. 1 and 2, one or more embodiments or implementations of the present invention are hereinafter described in conjunction with the drawings with like reference numerals being used to refer to like elements throughout, where the illustrated structures are not necessarily drawn to scale. A method 100 is illustrated in FIG. 1 for determining a transfer characteristic of a welding consumable or a material used in the manufacture thereof, and FIG. 2 shows an exemplary system 200 in accordance with the invention. The exemplary method 100 is illustrated and described below as a series of acts or events. However, the methods of the present invention are not limited by the illustrated ordering of such acts or events. For example, some acts may occur in different orders and/or concurrently with other acts or events apart from those illustrated and/or described herein, in accordance with the invention. In addition, not all illustrated steps may be required to implement a method in accordance with the present invention. Furthermore, the methods of the invention may be carried out in association with various test systems and welding consumables and constituent materials illustrated and described herein, as well as in association with other systems and test articles that are not illustrated or specifically discussed. In this regard, the methods may be employed with any materials or welding consumable final or intermediate product, referred to hereinafter as welding consumable test items.

FIG. 2 shows one suitable system 200 in which the method 100 may be carried out, including an environmental test chamber 210 with an interior or inside 212 defined by sidewalls, a top, and a bottom, with a door 214 providing access to the chamber interior 212. Chamber 210 also includes a control system 216 with various temperature and humidity components (e.g., heating coils, air circulation devices, pumps, cooling elements, gas supplies, etc., not shown) to provide controllable regulation of the interior 212 at selectable temperature, pressure, humidity, and gas content settings with door 214 closed, as well as sensors or other feedback components (not shown) to measure the actual humidity, pressure, temperature, atmospheric material content, etc., of the chamber interior 212. Control system 216 may include any form of user interface devices, such as knobs, displays, network interfaces, etc. for manual or electronic adjustment of setpoint values and control schemes, and provides for actuation of heating, cooling, pressure control, gas supply, and other control elements associated with chamber 210 in closed loop fashion according to one or more setpoint values and feedback process variables. In addition to fixed value regulation, control system 216 may be adapted to provide for regulation of one or more environmental variables through any suitable control techniques or algorithms, including but not limited to ramping setpoint values, ramp and soak techniques, etc. Chamber 210 is also equipped with a feedthrough port 218 for passing one or more electrical signals through the back wall, in this case including a cable connector for connection of communications cables between devices inside the chamber interior 212 and other apparatus outside chamber 210. Ideally, the chamber sidewalls, door 214, and feedthrough 218 are hermetically sealed or otherwise adapted to provide sufficient sealing with door 214 closed such that the control system 216 and the apparatus associated therewith can regulate and control the atmospheric conditions within chamber interior 212. In particular, the exemplary control system 216 of chamber 210 is operable to control humidity, temperature, nitrogen, and/or $CO_2$ content in the interior 212 of chamber 210 while a plurality of weight measurements are taken, wherein system 200 forms an exemplary embodiment of a test system in accordance with one or more aspects of the invention.

A weight measurement instrument is located in the chamber interior 212, in this case an analytical balance or scale 220 positioned on the chamber floor and operable to measure the weight of a welding consumable test item 240 placed on a specimen tray 222 thereof. Alternatively, the weight measurement instrument 220 could be placed on a table, stand, or other support structure within interior 212 of chamber 210, wherein all such arrangements are contemplated as falling within the scope of the invention and the appended claims. Suitable instruments 220 include analytical balance instruments such as those marketed by the Mettler Toledo company of Columbus, Ohio, although any measurement apparatus can be used which operates to obtain a plurality of measurements of the weight, mass, resistivity, length, or other property, feature, or characteristic of a tested sample within chamber interior 212 at different times, where the instrument 220 is preferably suitable for operation at tested environmental conditions within the test chamber 210. The illustrated analytical balance instrument 220 includes a glass case 224 with one or more openable panels allowing test samples (e.g., welding electrode section 240) to be placed on tray 222, wherein the glass enclosure 224 allows passage or particulate matter and gases therethrough, whereby the atmospheric conditions at instrument tray 222 (e.g., the pressure, temperature, humidity, and material content conditions at the tested electrode 240) are controlled to the test condition by the chamber environmental control system 216. Alternatively, a weight measurement instrument may be used with enclosure 224 omitted, or other types of enclosures or cases can be used, such as metal or steel, for example. The instrument 220, moreover, includes a communications port 226 for connection of a data cable 228 to the chamber feedthrough 218, such that instrument 220 can communicate with or otherwise provide measurements to a processing device outside chamber 200. In the illustrated implementation, balance instrument 220 includes an RS-232C data communications port 226 providing serial communications via cable 228.

The measurement system 200 in FIG. 2 also includes a computer 230 with data acquisition software and a serial data communications interface 232 connected by a serial cable 234 to a mating connector of feedthrough 218 (not shown) on the outside of the back wall of chamber 210, whereby computer 230 and data acquisition software thereof are operatively connected with weight measurement instrument 220 to obtain a plurality of test item weight measurements at different times while the atmospheric condition in chamber interior 212 is controlled to a test condition.

Using the arrangement of system 200, therefore, the tested welding consumable 240 can be environmentally evaluated by exposure to a given set of atmospheric conditions, with weight measurements being obtained periodically or continuously in substantially real time without disturbing the atmospheric condition in the interior 212 of chamber 210, wherein the weight measurements obtained thereby can be used to characterize or quantify material transfer characteristics of welding consumable test items. It is noted that unlike the conventional measurement techniques and systems, the tested article 240 need not be removed from the chamber 210 and indeed chamber door 214 can remain closed while weight measurements are taken. Moreover, the tested sample electrode section 240 need not be handled or moved for weight measurements to be taken. In this regard, any suitable processing device 230 may be employed, wherein the illustrated computer is merely one suitable example. It is also noted that although a section of welding electrode 240 is shown in FIG. 2, any welding consumable test item may be tested according to the methods of the invention, including but not limited to welding electrodes (e.g., cored, solid, etc.), welding flux, powders used in forming electrode coatings, metals used in producing cored or solid welding electrodes, materials used in creating fillers for cored electrodes, etc., wherein granular or powder material being evaluated may be positioned on tray 222 directly or within a dish or other suitable container or structure within the chamber interior 212 in such a manner to allow weight measurements of the test item 240 using the instrument 220.

The method 100 is hereinafter described with references to system 200 of FIG. 2 for measuring a moisture transfer characteristic (e.g., moisture absorption) of the welding electrode sample 240. Method 100 begins at 110 in FIG. 1, with atmospheric conditions (e.g., humidity, temperature, $CO_2$ content, etc.) in the interior 212 of environmental chamber 210 being adjusted or otherwise set or controlled to a test condition (e.g., predetermined values or value ranges or value profiles (e.g., ramps) of temperature, humidity, pressure, etc., in one example). At 120 the consumable test item or sample 240 is located on the scale or balance instrument 220 (e.g., on tray 222) in chamber 210 and chamber door 214 is closed at 130. As noted above, the ordering of acts shown in FIG. 1 is exemplary, although setting the chamber interior 212 to the test conditions at 110 prior to introducing the test specimen 240 to the atmospheric conditions and closing the chamber at 120 and 130, respectively, may advantageously allow measurement of any short-term effects caused by a rapid change in environment, which may be of particular interest if the welding consumable is actually used in similar situations involving rapid environmental change. An initial weight measurement is taken at 140, with the balance instrument 220 within the controlled-atmosphere of chamber 210, where instrument 220 transmits data to the data collection processing device 230 outside the chamber 210 via cables 228, 232, and feedthrough 218. Testing continues at 150 and 160 in the method 100, with further weight measurements being obtained at 150 until the test duration has been completed (YES at 160), after which the tested consumable sample 240 can be removed from chamber 210 at 170.

Figure 3:
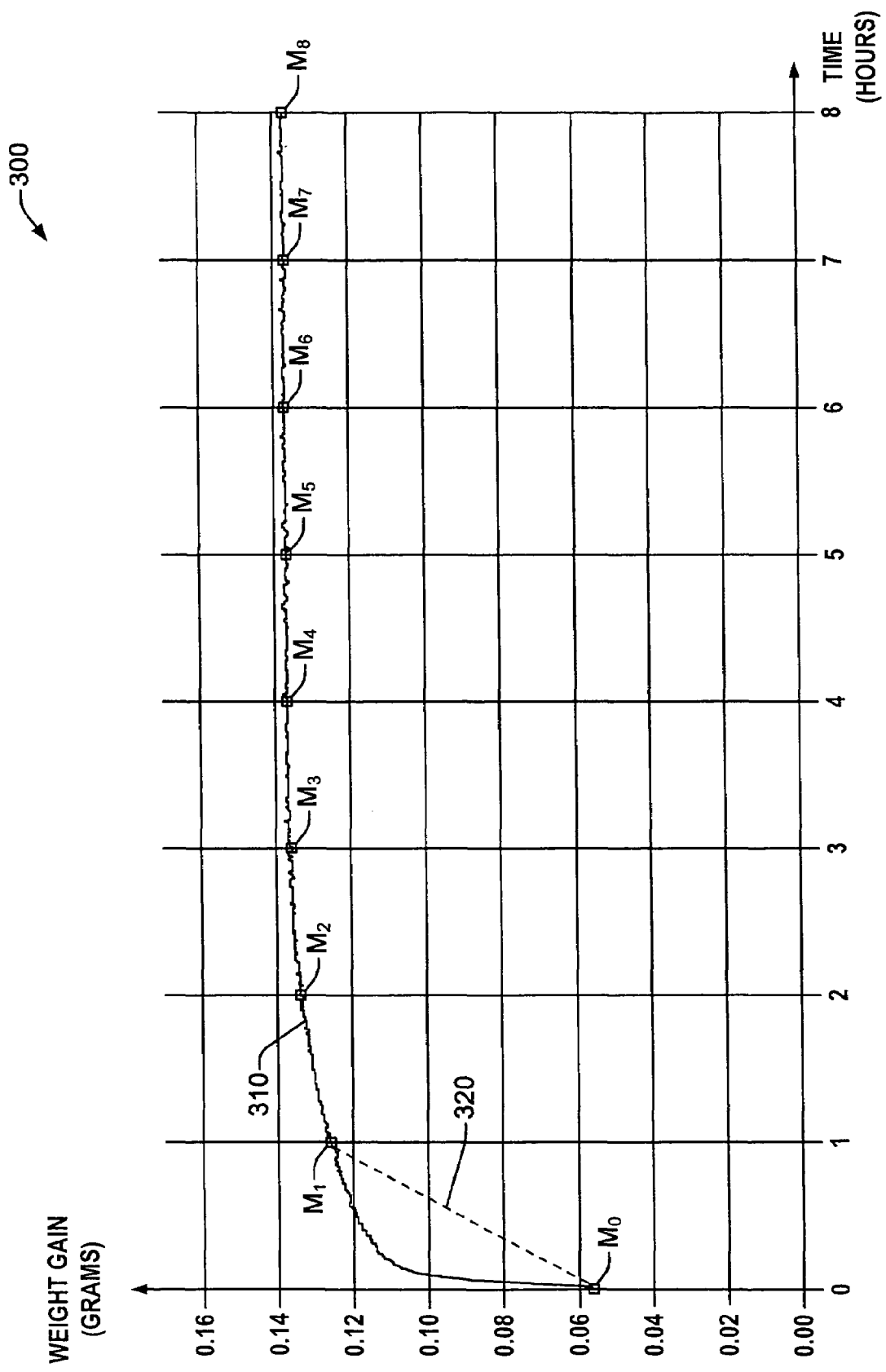
FIG. 3 is a graph showing an exemplary moisture absorption curve for welding electrodes in a humid environment.

A graph 300 is provided in FIG. 3 showing an exemplary moisture absorption curve 310 plotted as weight gain (grams) vs. time (hours) over an eight hour test duration for a single welding electrode with measurements taken at 5 second intervals using the systems and methods described above. Also shown are several measurements $M_0$ through $M_8$ taken at the start of the testing and at one hour intervals thereafter, such as might be taken in the conventional testing approach described above using eight separate test samples with a sample being removed from the test chamber every hour for measurement. As can be seen from the measurement curve 310 in FIG. 3, the exemplary systems and methods of the invention allow collection of real-time moisture absorption or release properties (or other material transfer characteristics, e.g., $CO_2$ absorption or release) in a variety of atmospheres, where the weight measurements can be taken and the corresponding measurement data can be acquired periodically or continuously to provide high time resolution to capture both short-term and long-term material transfer characteristics of a tested welding consumable 240. FIG. 3 also shows an example of an interpolated line 320 showing assumed absorption data between the conventional measurements $M_0$ and $M_1$, wherein comparison of the curves 310 and 320 shows the superiority of the techniques of the present invention in identifying the true short-term moisture transfer characteristics of the tested welding electrode 240. In this regard, compared with conventional welding consumable testing techniques discussed above, the invention provides a number of advantages over traditional time-based measurements, including reduction in the number of tests required for adequate data spreading, reduced testing cost and time, reduced levels of test personnel oversight, reduction in the amount of samples required to obtain multiple measurements, as well as improvements in the time resolution of the acquired data and improved testing accuracy. Moreover, the entire test process may optionally be automated, for instance, with control system 216 and computer 230 being operatively coupled and with computer 230 being programmed to implement one or more preprogrammed tests while providing setpoint values to control system 216 for controlling the atmospheric conditions within interior 212 of test chamber 210. Other variant implementations are possible, including adaptation of chamber 210 to provide controllable amounts of $CO_2$ and/or nitrogen or other material of interest for measuring absorption (or release) thereof by a welding consumable or material used in fabricating welding consumables, wherein all such alternative embodiments are contemplated as falling within the scope of the present invention and the appended claims.

The invention has been illustrated and described with respect to one or more exemplary implementations or embodiments, although equivalent alterations and modifications will occur to others skilled in the art upon reading and understanding this specification and the annexed drawings. In particular regard to the various functions performed by the above described components (assemblies, devices, systems, circuits, and the like), the terms (including a reference to a "means") used to describe such components are intended to correspond, unless otherwise indicated, to any component which performs the specified function of the described component (i.e., that is functionally equivalent), even though not structurally equivalent to the disclosed structure which performs the function in the illustrated implementations of the invention. In addition, although a particular feature of the invention may have been disclosed with respect to only one of several implementations, such feature may be combined with one or more other features of the other implementations as may be desired and advantageous for any given or particular application. Also, to the extent that the terms "including", "includes", "having", "has", "with", or variants thereof are used in the detailed description and/or in the claims, such terms are intended to be inclusive in a manner similar to the term "comprising".

The following is claimed:

1. A method for determining a transfer characteristic of a welding consumable or material used in fabricating welding consumables, said method comprising:

providing a measurement instrument within an environmental chamber;

adjusting the atmospheric condition in the interior of said environmental chamber to a test condition;

providing a test item on said instrument within the interior of said chamber, said test item being a coating for a coated welding electrode;

measuring an initial characteristic of said test item using said instrument; and taking a plurality of measurements of said test item at different times using said instrument while controlling the atmospheric condition in the interior of said environmental chamber to said test condition to determine a transfer characteristic of said test item.

2. A method as defined in claim 1, further comprising:

closing said environmental chamber prior to measuring the initial characteristic of said test item; and maintaining the chamber closed until after a final characteristic measurement.

3. A method as defined in claim 2, wherein said transfer characteristic of said test item is a moisture transfer characteristic, and wherein the interior of said chamber is controlled to a test humidity condition while taking said plurality of measurements.

4. A method as defined in claim 2, wherein the temperature of the interior of said cabinet is controlled while taking said plurality of measurements.

5. A method as defined in claim 1, wherein said transfer characteristic of said test item is a moisture transfer characteristic, and wherein the interior of said chamber is controlled to a test humidity condition while taking said plurality of measurements.

6. A method as defined in claim 5, wherein the temperature of the interior of said cabinet is controlled while taking said plurality of measurements.

7. A method as defined in claim 1, wherein the temperature of the interior of said cabinet is controlled while taking said plurality of measurements.

8. A method as defined in claim 1, wherein said measurement instrument is a weight measurement instrument, and wherein measuring an initial characteristic of said test item comprises measuring an initial weight of said test item.

* * * * *